(12) United States Patent
Garfield et al.

(10) Patent No.: US 8,606,371 B2
(45) Date of Patent: Dec. 10, 2013

(54) UTERINE ELECTRICAL STIMULATION SYSTEM AND METHOD

(75) Inventors: Robert E. Garfield, Goodyear, AZ (US); Harvey Carp, Portland, OR (US); William L. Maner, Phoenix, AZ (US)

(73) Assignee: Dignity Health, San Francisco, CA (US)

( * ) Notice: Subject to any disclaimer, the term of this patent is extended or adjusted under 35 U.S.C. 154(b) by 393 days.

(21) Appl. No.: 12/756,064

(22) Filed: Apr. 7, 2010

(65) Prior Publication Data

US 2010/0286735 A1    Nov. 11, 2010

Related U.S. Application Data

(60) Provisional application No. 61/167,465, filed on Apr. 7, 2009, provisional application No. 61/250,802, filed on Oct. 12, 2009.

(51) Int. Cl.
*A61N 1/00* (2006.01)

(52) U.S. Cl.
USPC .................................. 607/138; 607/3; 607/39

(58) Field of Classification Search
USPC ........................................... 607/1–3, 39, 138
See application file for complete search history.

(56) References Cited

U.S. PATENT DOCUMENTS

| | | | |
|---|---|---|---|
| 3,589,370 A | 6/1971 | McDonald | |
| 5,964,789 A | 10/1999 | Karsdon | |
| 6,356,777 B1 | 3/2002 | Garfield et al. | |
| 6,694,192 B2 * | 2/2004 | Policker et al. | 607/115 |
| 6,735,476 B2 | 5/2004 | Mellen | |
| 6,741,895 B1 * | 5/2004 | Gafni et al. | 607/138 |
| 6,879,858 B1 | 4/2005 | Adams | |
| 2003/0055465 A1 | 3/2003 | Ben-Haim et al. | |
| 2007/0055337 A1 | 3/2007 | Tanrisever | |

FOREIGN PATENT DOCUMENTS

WO    WO 98/10831 A1    3/1998

OTHER PUBLICATIONS

Ogurtsov et al, Development of a specialized pacemaker for use in obstetrics and gynecology, 1987, Plenum Publishing Corporation, pp. 201-204.*

The Prevention and Management of Postpartum Haemorrhage: Report of Technical Working Group, Geneva Jul. 3-6, 1989. Geneva: World Health Organization, 1990.

Elbourne DR, Prendiville WJ, Carroli G, Wood J, McDonald S. Prophylactic use of oxytocin in the third stage of labour. Cochrane Database Syst Rev 2001;(4):CD001808.

Bais JM, Eskes M, Pel M, Bonsel GJ, Bleker OP. Postpartum haemorrhage in nulliparous women: incidence and risk factors in low and high risk women. A Dutch population-based cohort study on standard (>= 500mL) and severe (>= 1000mL) postpartum haemorrhage. Eur J Obstet Gynecol Reprod Biol 2004;115:166-72.

(Continued)

*Primary Examiner* — Niketa Patel
*Assistant Examiner* — William Levicky
(74) *Attorney, Agent, or Firm* — Quarles & Brady LLP

(57) ABSTRACT

Some embodiments of the invention provide a system and method for treating insufficient uterine contractions after labor and delivery. The system includes a control module and a current source controlled by the control module to produce stimulating current at a frequency greater than or equal to about 5.0 Hertz. The system also includes one or more stimulation electrodes to provide the stimulating current to the patient in order for the patient to produce tonic uterine contractions.

9 Claims, 10 Drawing Sheets

(56) References Cited

OTHER PUBLICATIONS

Reyal F, Deffarges J, Luton D, Blot P, Oury JF, Sibony O. Severe post-partum hemorrhage: descriptive study at the Robert-Debre Hospital maternity ward [French]. J. Gynecol Obstet Biol Repord (Paris) 2002;31:358-64.

Fawcus S, Mbizvo M, Lindmark G, Nyström L. A community-based investigation of maternal mortality from obstetric haemorrhage in rural Zimbabwe. Maternal Mortality Study Group. Trop Doct. Jul. 1997;27(3):159-63.

Norris TC. Management of postpartum hemorrhage. Am Fam Physician. Feb 1, 1997;55(2):635-40.

Sultatos LG. Mechanisms of drugs that affect uterine motility. J Nurse Midwifery. Jul-Aug 1997;42(4):367-70.

Alexander E. Weingarten, MD, Jeffrey I. Korsh, MD, George G. Neuman, MD, and Steven B. Stern, MD. Postpartum Uterine Atony after Intravenous Dantrolene. Anesth Analg 1987; 66:269-270.

Hacker, Neville, J. G. Moore, and Joseph Gambone. Essentials of Obstetrics and Gynecology. 4th ed. vol. 1. Philadelphia: Elsevier Inc., 2004. 151.

Rizvi F, Mackey R, Barrett T, McKenna P, Geary M. Successful reduction of massive postpartum haemorrhage by use of guidelines and staff education. BJOG 2004; 111:495-8.

Goer 1995, 58, 64 and Molloy, B.G., Sheil, O., and Duignan, N. M. Delivery after caesarean section: review of 2176 cases. Br. Med J 294.1987:1645-1647.

Reynolds SRM.The effect of certain calcium salts on the rhythmically contracting and quiescent uterine fistula, with observations on the action of posterior pituitary extracts. Am J Physiol —Legacy Content, vol. 105, Issue 2, 358-365, Jul. 31, 1933.

Svanström MC, Biber B, Hanes M, Johansson G, Näslund U, Bälfors EM. Signs of myocardial ischaemia after injection of oxytocin: a randomized double-blind comparison of oxytocin and methylergometrine during Caesarean section. Br J Anaesth. May 2008;100(5):683-9. Epub Apr 2, 2008.

Thomas JS, Koh SH, Cooper GM. Haemodynamic effects of oxytocin given as i.v. bolus or infusion on women undergoing Caesarean section. Br J Anaesth. Jan 2007;98(1):116-9. Epub Dec 2, 2006.

Chong YS, Su LL, Arulkumaran S. Current strategies for the prevention of postpartum haemorrhage in the third stage of labour. Curr Opin Obstet Gynecol. Apr. 16, 2004.(2):143-50. Review.

Catanzarite V, Gambling D, Bird LM, Honold J, Perkins E. Respiratory compromise after MgSO4 therapy for preterm labor in a woman with myotonic dystrophy: a case report. J Reprod Med. Mar 2008 ; 53(3):220-222.

Sanderson JB. The Electrical Response to Stimulation of Muscle, and its Relation to the Mechanical Response. J Physiol. May 20, 1895 ; 18(1-2):117-160.7.

Gordon T, Mao J. Muscle atrophy and procedures for training after spinal cord injury. Phys Ther. Jan. 1994;74 (1):50-60.

Lucas CM, van der Veen FH, Grandjean PA, Penn OC, Wellens HJ. What is the ideal pulse frequency for skeletal muscle stimulation after cardiomyoplasty? Pacing Clin Electrophysiol. May 1991;14(5 Pt 1):778-82.

Gould JC, Dholakia C. Robotic implantation of gastric electrical stimulation electrodes for gastroparesis. Surg Endosc. Jul 15, 2008.

Shafik A, El Sibai O, Shafik AA, Ahmed I, Mostafa RM. Vesical pacing: pacing parameters required for normalization of vesical electric activity in patients with overactive bladder. Front Biosci. Jan 1, 2004;9:995-9.

Morone MA Feuer H. The use of electrical stimulation to enhance spinal fusion. Neurosurg Focus. Dec 15, 2002;13(6):e5.

Marzioni D, Tamagnone L, Capparuccia L, Marchini C, Amici A, Todros T, Bischof P, Neidhart S, Grenningloh G, Castellucci M . Restricted innervation of uterus and placenta during pregnancy: evidence for a role of the repelling signal Semaphorin 3A. Dev Dyn. Dec. 2004;231(4):839-48.

Am J Obstet Gynecol. Morizaki N, Morizaki J, Hayashi RH, Garfield RE. A functional and structural study of the innervation of the human uterus.Jan. 1989;160(1):218-28.

Hollingsworth M. Mechanical responses of rat isolated uterine horns to transmural stimulation.Br J Pharmacol. Sep. 1975;55(1):41-6.

Hughes SJ, Hollingsworth M. Relaxin as a relaxant of the isolated rat uterus: comparison with its mechanism of action in vivo. Gen Pharmacol. Nov. 1997;29(5):829-33.

Gregory CM, Dixon W, Bickel CS. Impact of varying pulse frequency and duration on muscle torque production and fatigue. Muscle Nerve. Apr. 2007;35(4):504-9.

Cairns SP, Chin ER, Renaud JM. Stimulation pulse characteristics and electrode configuration determine site of excitation in isolated mammalian skeletal muscle: implications for fatigue. J Appl Physiol. Jul. 2007;103(1):359-68. Epub 2007 Apr 5. Erratum in: J Appl Physiol. Jan. 2008;104(1):319.

Webster JG. Design of cardiac pacemakers. IEEE Press. 1995.

Galuschky CW, Webster JG. Med Biol Eng Comput. Mar. 1998;36(2):233-7. Dual-chamber cardiac pacemaker tester.

Morizaki N, Morizaki J, Hayashi RH, Garfield RE. Am J Obstet Gynecol. Jan. 1989;160(1):218-28. A functional and structural study of the innervation of the human uterus.

International Search Report for PCT/US10/30302, dated Nov. 10, 2010.

\* cited by examiner

O – current turned on
X – current turned off

UTERINE ELECTRICAL STIMULATION SYSTEM AND METHOD

RELATED APPLICATIONS

This application claims priority under 35 U.S.C. §119 to U.S. Provisional Patent Application Nos. 61/167,465 filed on Apr. 7, 2009 and 61/250,802 filed on Oct. 12, 2009, the entire contents of which are incorporated herein by reference.

BACKGROUND

Postpartum hemorrhage, which is a significant source of maternal morbidity and mortality in modern obstetrics, occurs in up to 18 percent of births (1, 2). Even with appropriate management, approximately 3-4 percent of vaginal deliveries result in severe postpartum hemorrhage in the United States (3), which can result in occult myocardial ischemia, dilutional coagulopathy, and death (4). While sudden death can occur from rapid and uncontrolled postpartum hemorrhage because of brisk blood loss, many deaths are the result of ineffective management of continuous low-level bleeding (5). In less-developed countries and in rural areas of the United States, maternal hemorrhage is a greater issue. For example, in Zimbabwe, hemorrhage is responsible for 25 percent of maternal deaths. Approximately 125,000 women per year die worldwide due to postpartum hemorrhage (6).

Uterine atony causes more than 90 percent of cases of postpartum hemorrhage (5). Uterine atony is a loss of tone in the uterine musculature postpartum, resulting in the failure of uterine muscles to contract tonically and stop postpartum bleeding. This may be related to the inability of myometrial cells in some patients to act properly as pacemakers for tonic contractions after delivery (7), or may be related to changes in threshold or resting potentials brought on by the delivery process or by administration of medications (8).

Normally, contraction of the uterine muscle compresses the vessels and reduces blood flow after delivery. This increases coagulation, which prevents bleeding. However, lack of uterine muscle contractions can cause an acute postpartum hemorrhage. Many factors can contribute to the loss of uterine muscle tone, including overdistention of the uterus, multiple gestations, polyhydramnios, fetal macrosomia, prolonged labor, oxytocin augmentation of labor, grand multiparity (having given birth 5 or more times), precipitous labor (labor lasting less than 3 hours), magnesium sulfate treatment of preeclampsia, chorioamnionitis, halogenated anesthetics, and uterine leiomyomata (9).

Current treatments for preventing blood loss during uterine atony and/or uterine rupture include radical procedures such as surgery, manual massage, which is often minimally effective, and drugs, such as oxytocin, prostaglandins, and ergot alkyloids. Oxytocin and other drug treatment is a common global application, however it is not well controlled and can have dangerous side effects for the mother.

SUMMARY

Some embodiments of the invention provide a method for treating insufficient uterine contractions after labor and delivery. The method may include generating electrical stimulating current signals at a frequency greater than or equal to about 5.0 Hertz and applying the electrical stimulating current signals to one of a cervix, a vagina, and a uterus to produce uterine tonic contractions.

Some embodiments of the invention provide a system for treating insufficient uterine contractions in a patient after labor and delivery. The system may include a control module which performs at least one of preprogrammed stimulation tasks and user-defined stimulation tasks and a current source controlled by the control module to produce stimulating current at a frequency greater than about 5.0 Hertz. The system may also include one or more stimulation electrodes coupled to one of a uterus, a cervix, a vaginal wall, and an abdominal wall of the patient to provide the stimulating current to the patient in order for the patient to produce tonic uterine contractions.

DETAILED DESCRIPTION

Figure 1:
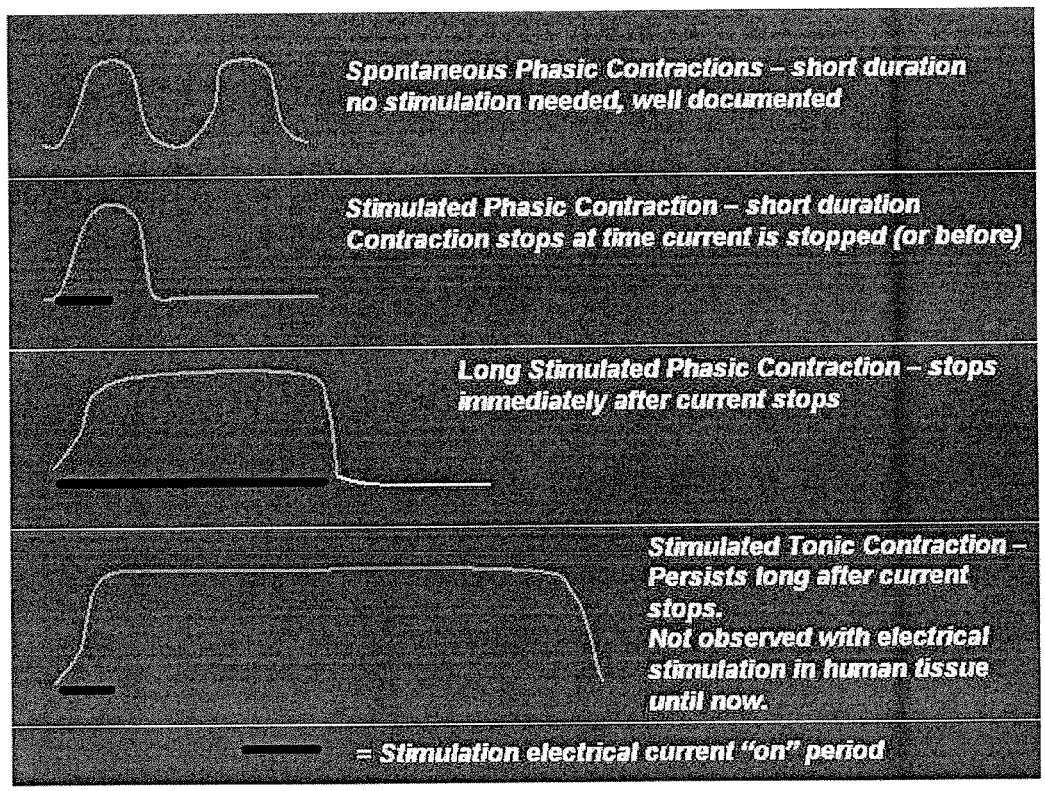
FIG. 1 illustrates different types of observable uterine contractile events.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings. Where appropriate, the terms "stimulation" and "stimulated" are understood to refer to electrical stimulation and electrically stimulated, respectively.

The following discussion is presented to enable a person skilled in the art to make and use embodiments of the invention. Various modifications to the illustrated embodiments will be readily apparent to those skilled in the art, and the generic principles herein can be applied to other embodiments and applications without departing from embodiments of the invention. Thus, embodiments of the invention are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of embodiments of the invention. Skilled artisans will recognize the examples provided herein have many useful alternatives and fall within the scope of embodiments of the invention.

Some embodiments of the invention provide a system and method of treating uterine atony by administering electrical stimulation to the uterus. The electrical stimulation to the uterus can result in uterine muscle contractile activity, which can aid in decreasing and/or stopping uterine bleeding.

Figure 2:
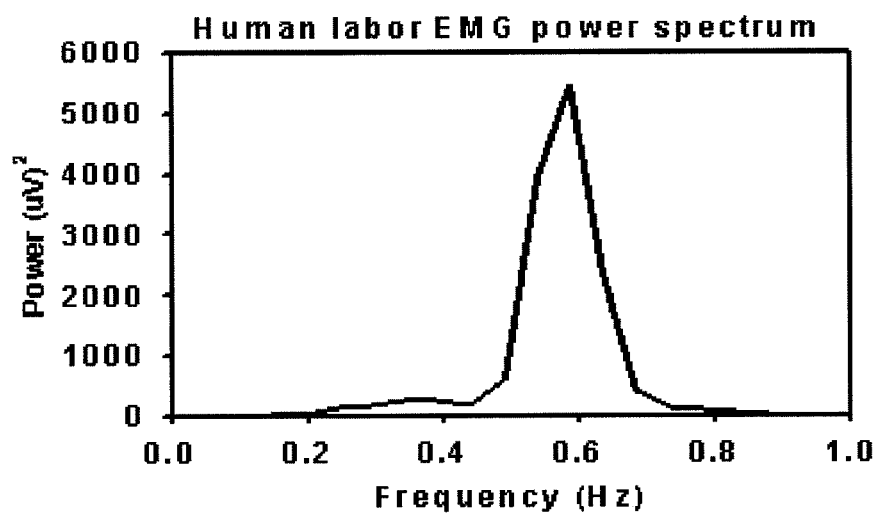
FIG. 2 is a graph illustrating a measured power of contracting uterine muscles at different action potential frequencies.

There are several different types of observable uterine contractile events. As shown in FIG. 1, some uterine contractile events can include spontaneous phasic contractions (spontaneous contractions which are short in duration and occur without outside stimulation), short stimulated phasic contractions (stimulated contractions which are shorter in duration and stop at or before the time stimulation is stopped), long stimulated phasic contractions (stimulated contractions which are longer in duration and stop immediately after the time stimulation is stopped), and tonic contractions (sustained contractions which persist long after stimulation is stopped). During labor and delivery, the human uterus exhibits spontaneous phasic contractions that produce associated electrical action potential frequencies in the range of 0.0 Hertz (Hz) to about 3.0 Hz. In addition, to a lesser degree, the human uterus also exhibits spontaneous phasic contractions during menstrual cycles in non-pregnant women. As shown in FIG. 2, electrical power output of uterine spontaneous phasic contractions is mostly concentrated at less than 1.0 Hz. Very little electrical power is observed in higher frequencies than the above-described range.

Current stimulation systems are used for stimulating the uterine tissue with similar frequencies as those seen naturally, using an external power source to induce contractions in laboring women who experience insufficient contractions to adequately deliver a baby. For example, U.S. Pat. No. 6,356, 777, the entire contents of which is incorporated herein by reference, specifies the use of electrical stimulating frequencies in the 0.0 Hz to about 5.0 Hz range for controlling phasic contractions. The uterus responds favorably to such electrical stimulation signals by exhibiting stimulated phasic contractions, like those occurring naturally during labor and delivery, as shown in FIG. 3.

Figure 3:
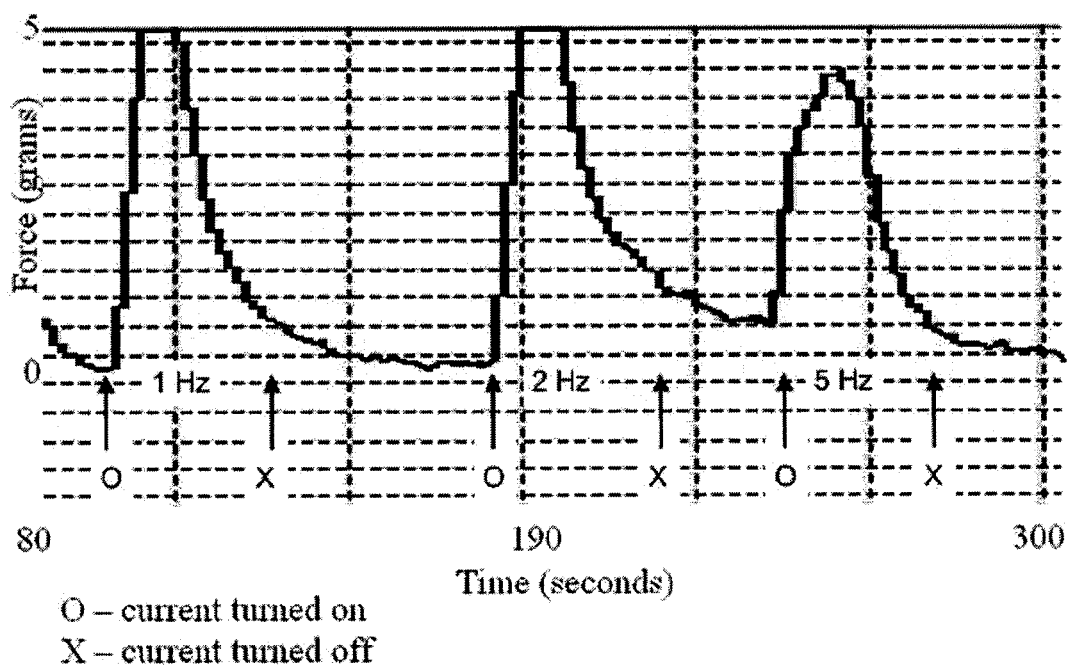
FIG. 3 is a graph illustrating forces exerted by contracting uterine muscles over time when stimulating current is applied at different frequencies.

FIG. 3 illustrates uterine muscle activity over time when a stimulation current is applied. As shown in FIG. 3, uterine muscle action returns to baseline immediately after the current is switched off when using frequencies up to about 5 Hz. In some instances, the maximal contractile activity begins to fall well before the current is turned off, which is indicative of stimulated phasic contractile activity. The stimulated phasic contractile activity shown in FIG. 3 can be considered short stimulated phasic contractions, as the stimulation duration is substantially small (e.g., less than about 3 minutes) and the stimulation frequency lies within the conventional uterine stimulation frequency range. In some embodiments, short stimulated phasic contractions can be specified as having a minimal duration time of about 30 seconds and a maximum duration time of about 3 minutes. Uterine muscle stimulation within these established ranges and the resulting phasic contractile activity are not thought to be useful for stopping uterine blood loss in the case of uterine rupture and postpartum hemorrhage.

Figure 4:
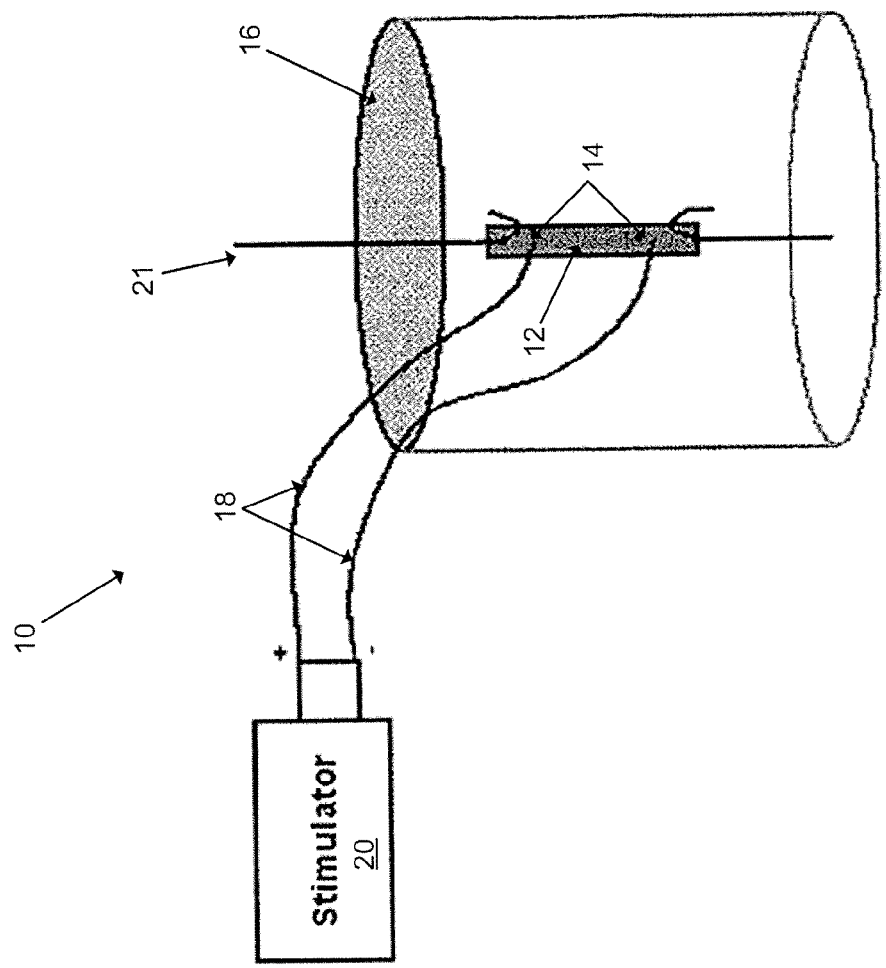
FIG. 4 is a schematic of an in vitro setup for stimulating uterine tissue and measuring resulting contractile activity.

FIG. 4 illustrates an in vitro setup 10 for stimulating uterine tissue and measuring resulting contractile activity. The setup includes one or more strips 12 (i.e., strips of uterine muscle tissue) outfitted with a plurality of stimulation electrodes 14 at each end (i.e., through suturing) isolated in a bath 16 of Kreb's solution. Electrode lead wires 18 are Teflon-coated so as to act as insulation from the Krebs solution to prevent shorting of electrical current. The setup 10 also includes a source 20 for providing electrical stimulation with varying parameters. Tension force of the strips are recorded using a transducer (e.g., force gauge 21) and a computer obtains force data sensed by the transducer for analysis and display. The following paragraphs describe force data obtained from setups similar to that described with reference to FIG. 4, using tissue of pregnant patients in labor or after delivery.

Figure 5:
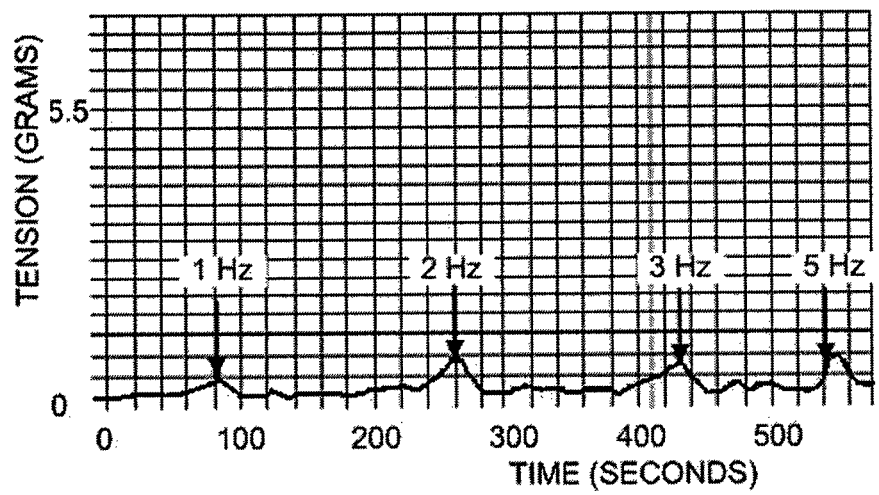
FIG. 5 is a graph illustrating a contractile recording of rat uterine tissue when varying frequency in applied stimulation current.
Figure 6:
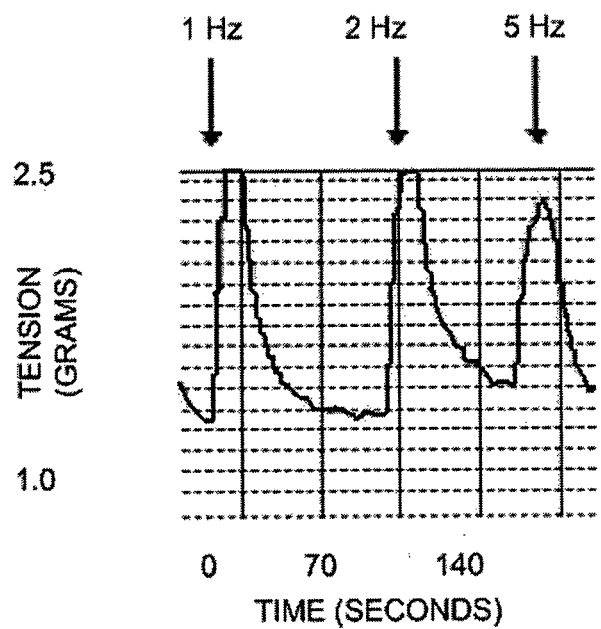
FIG. 6 is a graph illustrating a contractile recording of human uterine tissue, when varying frequency in applied stimulation current.
Figure 7:
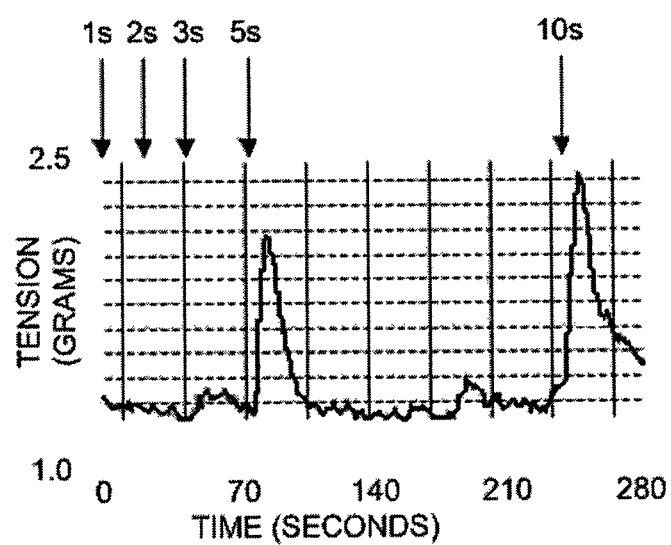
FIG. 7 is a graph illustrating a contractile recording of human uterine tissue, when varying train duration in applied stimulation current.

FIG. 5 illustrates resulting force data from a test strip 12 of rat uterine tissue, when varying the stimulation current frequency (at 1 Hz, 2 Hz, 3 Hz, and 5 Hz), with stimulation voltage and train duration fixed. Each frequency tested produced a visible contractile response, resulting in short stimulated phasic contractions. FIG. 6 illustrates resulting force data from a test strip 12 of human uterine tissue, with stimulation current frequency varied (at 1 Hz, 2 Hz, and 5 Hz), with stimulation voltage and train duration fixed. Each frequency tested produced a short stimulated phasic contraction. FIG. 7 illustrates resulting force data from a test strip 12 of human uterine tissue, with stimulation current train duration varied (at 1 second, 2 seconds, 3 seconds, 5 seconds, and 10 seconds), with stimulation voltage and frequency fixed. No noticeable response was seen from 1-second and 2-second train durations. However, train durations of 3 seconds, 5 seconds, and 10 seconds produced short stimulated phasic contractions. The short stimulated phasic contractions shown in FIGS. 5-7, while useful for inducing or augmenting labor in women whose uterine function is insufficient for successful labor and delivery, are not useful for stopping blood loss during uterine atony and postpartum hemorrhage.

Figure 8:
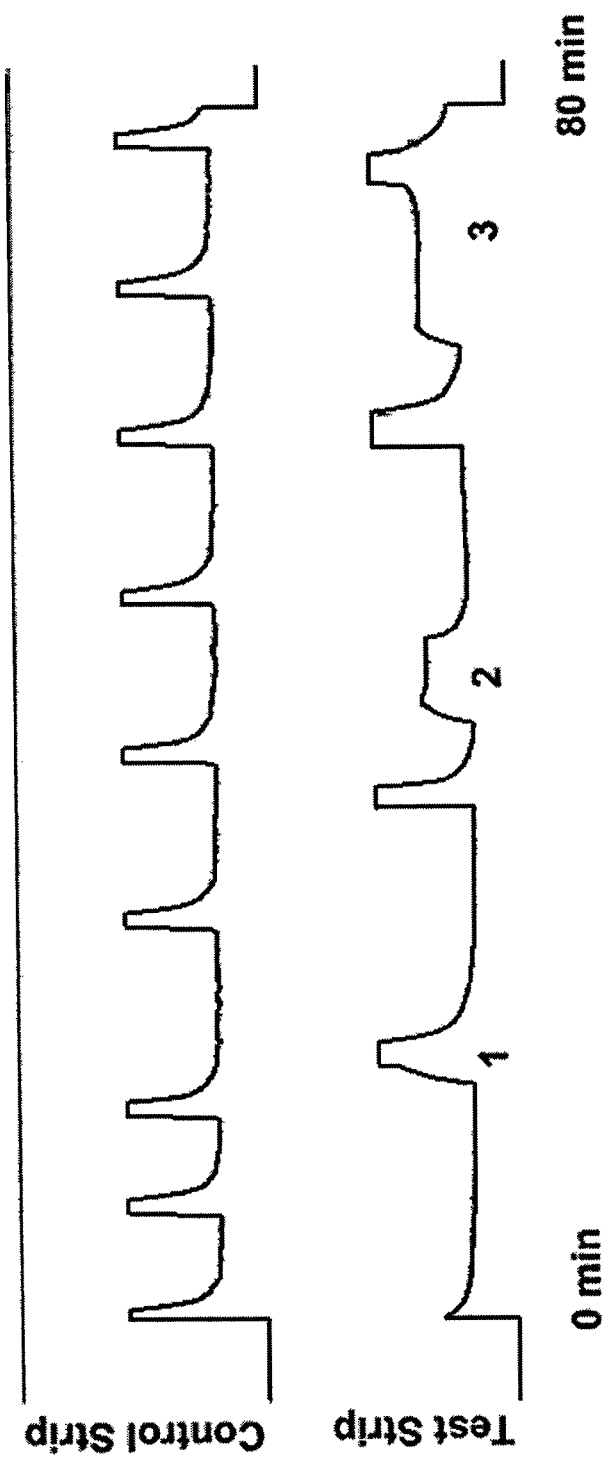
FIG. 8 is another graph illustrating contractile recordings of human uterine tissue, including a control trace and a test trace, when varying train duration in applied stimulation current.

FIG. 8 illustrates resulting force data from test and control strips 12 of human myometrial tissue that were obtained from a term patient (39 weeks gestation) who demonstrated insufficient contractile activity during labor. Electrical stimulation at about 10 volts in pulses of about 2 Hz were applied to the test strip 12. The pulses were run for a 5 minute duration (period 1), a 10 minute duration (period 2), and a 20 minute duration (period 3). FIG. 8 shows spontaneous phasic contractile activity in the control strip 12 (top trace, no outside electrical stimulation provided), and spontaneous phasic contractile activity as well as stimulated phasic contractile activity in the test strip 12 (bottom trace, outside electrical stimulation provided by the source 20). The test strip 12 produced stimulated phasic contractile activity during period 1, period 2, and period 3 as a result of direct electrical stimulation of the test tissue. The duration of the stimulated phasic contractile activity was in direct proportion to the duration of the electrical stimulation current applied, and when the electrical stimulation current was turned off, the test strip force measurement returned fully to baseline, illustrating complete relaxation of the tissue.

The stimulated phasic contractile activity shown in FIG. 8 can be considered long stimulated phasic contractions, as the stimulation duration is longer than about 3 minutes and the stimulation frequency lies within the conventional uterine stimulation frequency range. In some embodiments, long stimulated phasic contractions may be substantially effective for reducing bleeding during postpartum hemorrhage and uterine atony, however, the amount of electrical energy required, and the length of time that the uterine tissue is exposed to such energy, may be too large to be of practical value in other embodiments.

Figure 9:
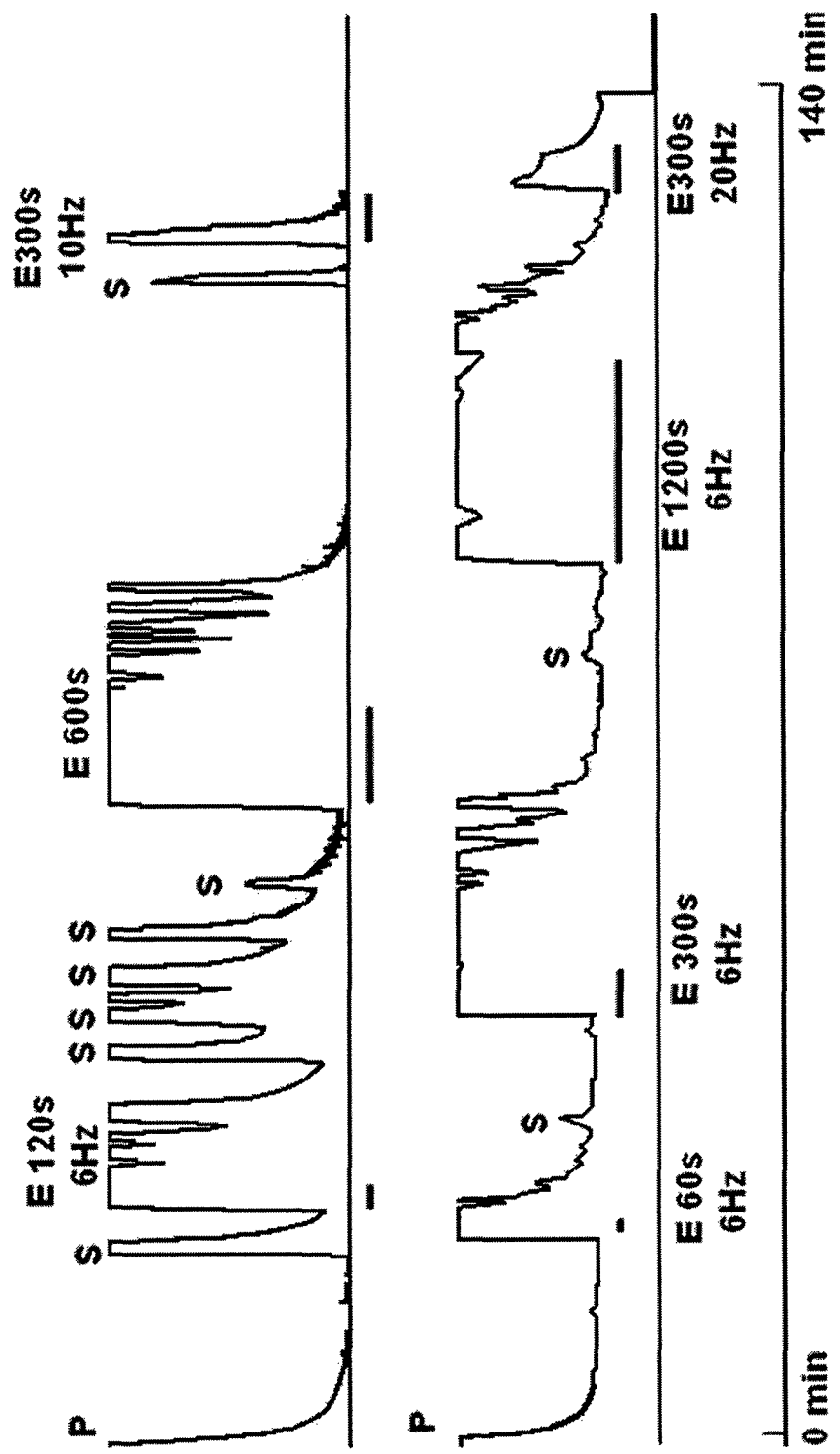
FIG. 9 is a another graph illustrating contractile recordings of human uterine tissue, when varying frequency outside conventional parameters in applied stimulation current, in accordance with one embodiment of the invention.

FIG. 9 illustrates resulting force data from two test strips 12 of human uterine tissue, with electrical stimulation frequencies varied (at 6 Hz, 10 Hz, 20 Hz) and with electrical stimulation current pulse train duration varied (at 60 seconds, 120 seconds, 300 seconds, 1200 seconds). Spikes shown in FIG. 9 indicate uterine muscle contractions. The spikes labeled "P" indicate initial preparatory contractions. The spikes labeled "S" indicate spontaneous uterine phasic contractions. The solid bars under the long spikes indicate the time periods during which electrical stimulation currents were applied to the uterine muscles. These time durations of electrical stimulation are indicated above the long spikes (in seconds) following the letter "E". While frequencies greater than or equal to about 5.0 Hz lie outside of the established range of frequencies normally associated with uterine electrical activity, they are capable of producing a muscle response in the form of sustained uterine contractions. These contractions can be considered tonic contractions (a type not observed during labor and delivery or using electrical stimulation on the uterus within established frequencies). As shown in FIG. 9, these tonic contractions remain forceful well after the treatment has stopped (i.e., after the applied electrical current has been turned off). In some embodiments, these tonic contractions (i.e., forceful and sustained contractions) or tetanic contractions (i.e., tonic contractions which remain maximally, or near-maximally, forceful) can be very useful for stopping blood loss during uterine atony and uterine rupture.

Tonic contractile events are not possible to achieve using conventional electrical stimulation parameters (i.e., 0.0 Hz to about 5.0 Hz), which only seem capable of producing phasic contractions of the type observed during labor and delivery. Also, presently available drugs and systems, including oxytocin, are not capable of producing sustained, forceful contractions after treatment with them has completed. In some embodiments, only tonic contractions, achieved using frequencies at or above about 5.0 Hz, can be useful for contracting the uterus during critical bleeding in women with uterine atony and/or uterine rupture. These types of contractions can help reduce the bleeding to allow doctors enough time to stabilize the patient with other methods (e.g., to suture the uterus if needed without having to perform more radical surgery, like a hysterectomy), or can help stop the bleeding completely on their own.

Figure 10:
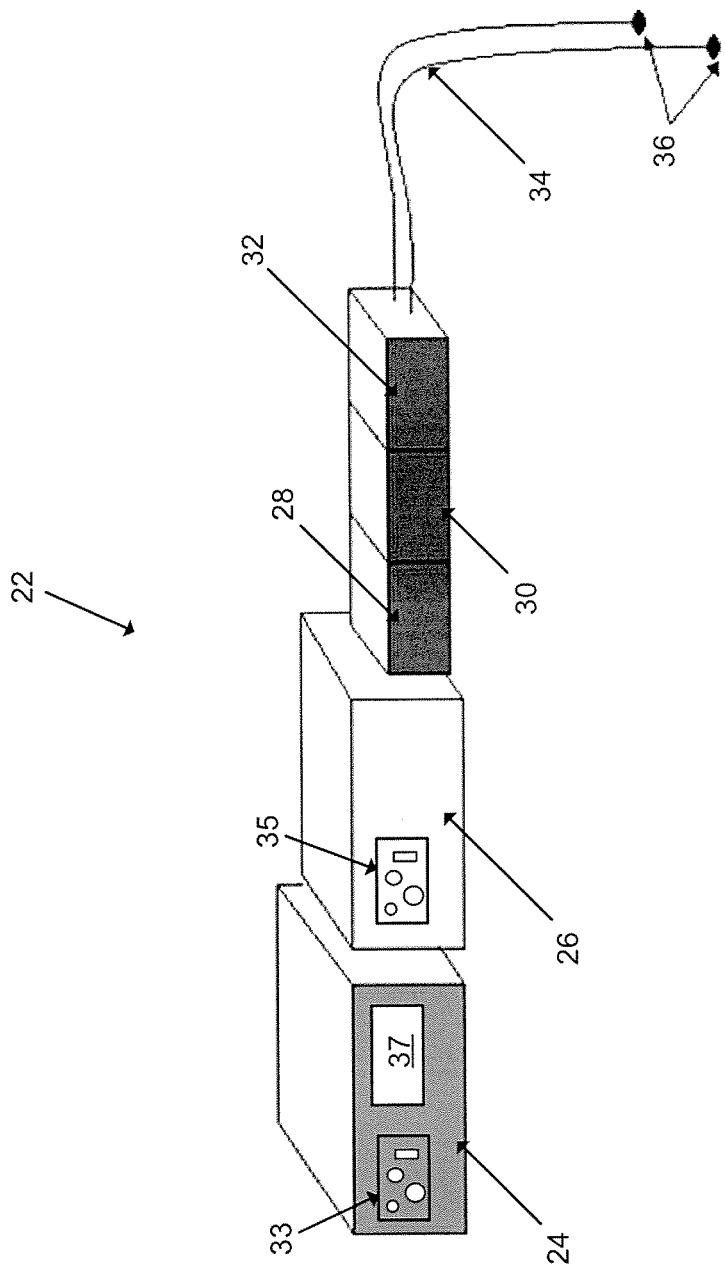
FIG. 10 is a schematic view of a system according to one embodiment of the invention.

FIG. 10 illustrates a system 22 according to one embodiment of the invention. The system 22 can stimulate uterine muscles into tonic contractions using frequencies greater than about 5.0 Hz. The system 22 can be used to stimulate muscles of the uterus in a way that does not affect other organs and can be accurately regulated and controlled, unlike oxytocin or other conventionally-used drugs. The system 22 can be used on a patient, such as a female post-partum, and can be controlled by a user, such as a physician or medical staff member. For example, the system 22 can input innocuous electrical pulses into the patient's uterus with sufficient effect to incite postpartum tonic or tetanic contractions in order to help treat uterine atony and postpartum hemorrhage. In some embodiments, the system 22 can include a control module 24, a current source 26, an isolation unit 28, a constant maximum current unit 30, a biphasic converter 32, a set of lead wires 34, and a set of electrodes 36.

The control module 24 can contain computing capability, software, and memory. The controlling module 12 can be set using interface controls 33, such as dials, switches and/or auxiliary inputs, to perform preprogrammed stimulation tasks, including commanding the current source 26 to output stimulation current of selected frequency, amplitude, pulse width, and train duration automatically for selected periods of time. The control module 24 can also be operated manually by the user, in which the user can determine and set one or more output stimulation currents of desired frequencies, amplitudes, pulse widths, and train durations as needed spontaneously (i.e., in real time or in near-real time). For example, the control module 24, can be operated automatically or manually to produce a stimulation current which can cause tonic or tetanic contractions of the patient's uterine muscle and the user has the capability to adjust the stimulation current parameters (i.e., frequencies, amplitudes, pulse widths, and/or train durations) in real time or near-real time during observation of the patient's uterus.

In one embodiment, the control module 24 can automatically or manually operate multiple stimulation outputs of the current source 26 independently or in unison with varying or similar current frequencies, amplitudes, pulse widths, and train durations. As a result, the control module 24 can provide stimulation currents directly to the uterus or through various organs, such as the cervix, vaginal wall and/or abdominal wall separately, simultaneously, or sequentially, or can provide stimulation currents to various parts of the uterus separately, simultaneously, or sequentially.

In one embodiment, pre-recorded uterine electrical traces, obtained from normally-contracting patients and saved digitally, can be stored in the control module 24 to be used, in turn, as the electrical current trace patterns for commanding the current source 26 to output identical stimulation current to patients with abnormal uterine activity, such as patients with insufficient or absent contractile activity during postpartum hemorrhage. In addition, artificially generated current traces, saved digitally, with known frequencies, amplitudes, pulse widths, and train durations, can be stored in the control module 24 to be used as the electrical current trace patterns for commanding the current source 26 to output identical stimulation current to patients with abnormal uterine activity during postpartum hemorrhage.

In another embodiment, the control module 24 can automatically regulate and modify the electrical current output produced by the current source 26 based on input from electrical contractile activity of the patient's uterus, which can be transmitted to the control module 24 via pick-up wires, a signal conditioner, and/or after-conditioning wires (not shown). The control module 24 can regulate and modify the produced electrical current by changing the electrical stimulation pulse-width, current amplitude, pulse train duration, and/or the pulse frequency according to a pre-programmed algorithm.

In some embodiments, the control module 24 can include a display 37, such as a video display, a digital display, light-emitting diode (LED) display, etc., to display the stimulation output currents produced for the user to read or assess. The control module 24 can be coupled to the current source 26 by wires, direct electrical coupling, or another suitable coupling.

For example, in one embodiment, the control module 24 can communicate with the current source 26 via a wireless connection, such as Bluetooth®.

The current source 26 can generate the output stimulation current. In one embodiment, the electrical stimulation current settings can be adjusted at the current source 26 by the user using interface controls 35, such as dials, switches or other settings. In another embodiment, the electrical stimulation settings can be controlled by the control module 24 (e.g., as preprogrammed settings or by the user using the interface controls 33, as described above), and output to the current source 26. As described above, in some embodiments, the current source 26 can output multiple electrical stimulation currents either directly to the uterus or indirectly to the uterus via the cervix, the vaginal wall and/or the abdominal wall separately, simultaneously, or sequentially, as commanded by the control module 24, or the current source 26 can output multiple electrical stimulation currents to various locations of the uterus separately, simultaneously, or sequentially.

In some embodiments, there can be a constant two-way communication between the current source 26 and the control module 24, so that the current source 26 can receive commands from the control module 24 and the control module 24 can receive actual output current values from the current source 26.

In some embodiments, the current source 26 can be capable of generating an output current between about 0.01 milliamperes and about 40.00 milliamperes (with possible voltages between about 0.0001 volts and about 100 volts). Pulse widths of the current can be adjusted between about 0.1 millisecond and about 1000 milliseconds. Frequencies of the current can be adjusted from about 0.1 Hertz to about 30 Hz or greater. Pulse train durations can be adjusted from about 1 second to about 10,000 seconds. In addition, output currents can be sinusoidal so as to reduce tissue damage and maximize effect (10). In one embodiment, the current source 26 can produce a maximal "jolt" of uterine electrical stimulation energy equivalent to between about 1 Joule and about 120 Joules of electrical energy in a short duration between about 1 millisecond and about 1000 milliseconds. Further, the electrical stimulation current output from the current source 26 can be sensed, measured, or detected by either the current source 26 or the control module 24 and can be automatically shut off if current values are determined to be dangerous or outside prescribed, programmed, or set values.

The isolation unit 28 can prevent ground loop currents from affecting the patient. In one embodiment, isolation is accomplished through optical isolation. In other embodiments, induction or other methods of isolation can be used by the isolation unit 28.

The constant maximum current unit 30 can allow the user to regulate the amount of maximum current that the patient's uterus receives. The constant maximum current unit 30 can prevent tissue damage due to extreme current fluctuations as tissue resistance varies (11), and can be set (either in a discrete or continuous fashion) to or between values well below human threshold for human feeling (e.g., about 0.01 milliamperes) and values uncomfortable for humans (e.g., about 10 milliamperes). In one example, the constant maximum stimulation current can be set at a value which maximizes current input without damaging tissue and with minimal discomfort to the patient (e.g., about 4 milliamperes).

The biphasic converter 32 can alternate the polarity of current pulses produced by the current source 26 after having moved through the isolation unit 28 and the constant maximum current unit 30 in order to further prevent adverse effects on the patient's tissues. The biphasic converter 32 can insure that the total energy delivered at the tissue site, as integrated over time, has a net value of zero. This can reduce the possibility of heating and subsequent damage to the patient's tissues (11, 12).

The lead wires 34 can transmit the output current from the biphasic converter 32 to the electrodes 36. In one embodiment, the lead wires 34 can be similar to those manufactured by Advantage Medical Cables. In some embodiments, the system 22 can include between one and ten lead wires 34. For example, different lead wires 34 can carry different types or strengths of currents that incite, induce, or augment a tonic contraction at different times in different parts of the uterus, as preprogrammed or set by the user (e.g., to stimulate various parts of the patient's uterus separately, simultaneously, and/or sequentially).

Figure 11:
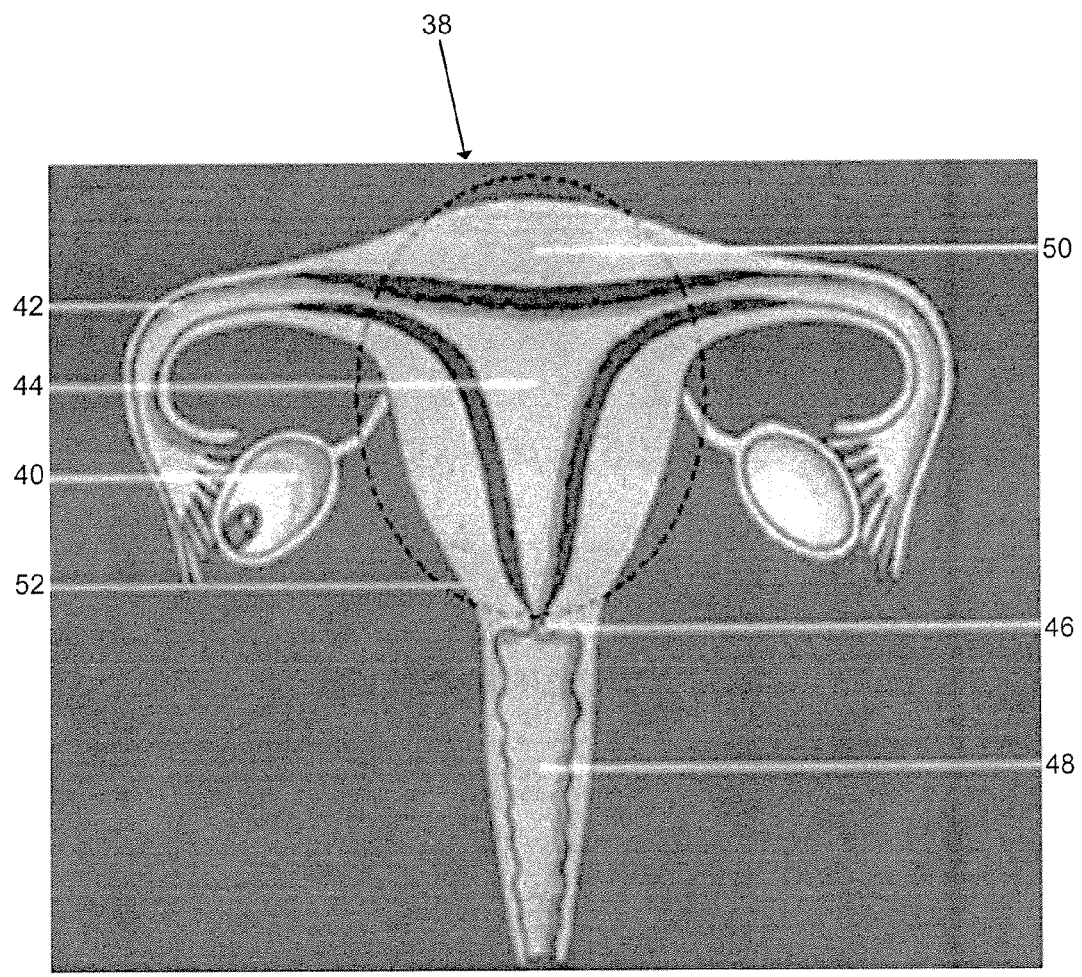
FIG. 11 is a front cross-sectional view of a uterus.

FIG. 11 illustrates a patient's uterus 38, ovaries 40, fallopian tubes 42, a uterine body (or intrauterine cavity) 44, a cervix 46, a vagina 48, a fundus 50 (i.e., top portion) of the uterus, and a distal portion 52 of the uterus. The electrodes 36 can be attached to or near the uterus 38 in a specific orientation and at specific locations that will have the best effect upon uterine contractility for the patient, as determined by the user. In one example, the electrodes 36 can be placed upon the vaginal wall 48 and/or the cervix 46. In another example, electrodes 36 can be placed at locations across the fundal 50 and distal portions 52 of the uterus 38. Also, the electrodes 36 can be mounted externally to the patient's abdominal surface.

The electrodes 36 can be attached to the patient's abdominal surface and/or uterus 38 using biocompatible glue or tissue adhesive, or by suction or other self-affixing electrodes. In one embodiment, the electrodes 36 can be standard silver chloride (AG2Cl) electrodes, EEG electrodes, suction electrodes, or needle electrodes. In some embodiments, the system 22 can include between one and ten electrodes 36 (e.g., equal to the number of lead wires 34). Different electrodes 36 can be positioned at various locations in or around the patient's uterus 38, where some or each of the electrodes 36 causes tonic and/or phasic effects according to the electrical stimulus applied through them. For example, one or several electrodes 36 can act as a local pacemaker for eliciting contractions, while one or several other electrodes 36 can cover one or many different portions of the uterus 38 for eliciting global tonic or tetanic contractions. In addition, in some embodiments, the electrodes 36 can consist of platinum-iridium metals, so as to reduce the possibility of tissue lesions (12).

Figure 12A:
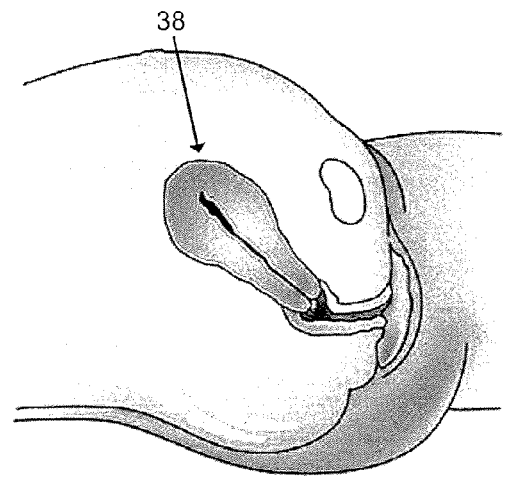
FIG. 12A is a side cross-sectional view of a uterus normally contracting post-partum.
Figure 12B:
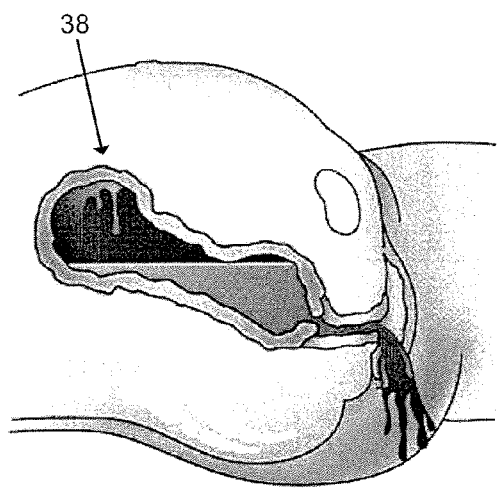
FIG. 12B is a side cross-sectional view of a ruptured uterus, which is not contracting post-partum due to uterine atony.
Figure 12C:
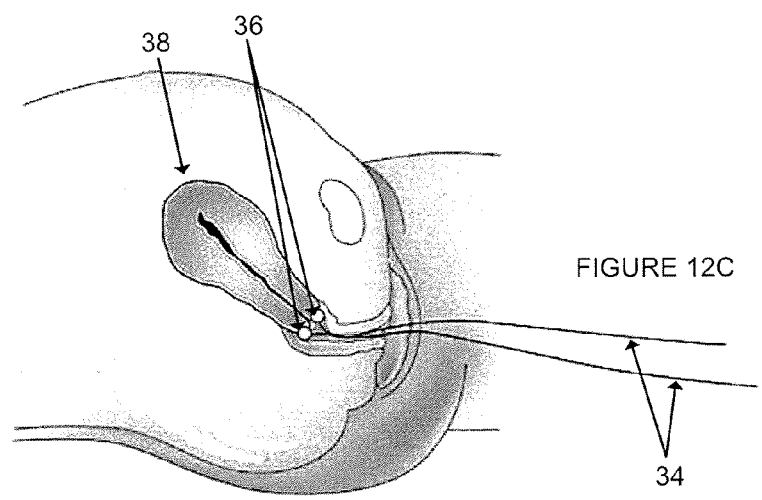
FIG. 12C is a side cross-sectional view of a ruptured uterus being stimulated by the system of FIG. 10.

FIGS. 12A-12C illustrate a patient's uterus 38 in three different conditions. FIG. 12A shows a naturally contracting uterus 38 post-partum. Forceful and spontaneous tonic contractions can prevent blood loss. FIG. 12B shows a uterus 38 which is not contracting postpartum due to uterine atony. The lack of tonic contractile activity allows the uterus to bleed out, threatening the life of the patient. FIG. 12C shows the uterus 38 with atony and uterine rupture treated effectively (i.e., forcefully contracted) using electrical tonic stimulation. As shown in FIG. 12C the uterus 38 has been outfitted with electrodes 36 (trans-vaginally) so that the system 22 can output stimulated current (i.e., through the lead wires 34) for tonic activity using electrical frequencies greater than or equal to about 5 Hz. The artificially-stimulated tonic contractions can help reduce, stop and/or manage the blood loss. In one embodiment, the stimulated current can be output to the patient for a duration greater than about 10 seconds. In some embodiments, the pulse train durations can be up to about 30 minutes long.

In addition, the system 22 can be used in conjunction with other devices, methods, systems, and treatments for postpartum hemorrhage, uterine atony, and bleeding or coagulation problems, including but not limited to oxytocin, prostaglandins, misoprostol, prepidil, ergot alkyloids, tamponades, balloon tamponades, sponges, clamps, manual uterine massage and manipulation, sutures, bio-compatible adhesives, cauterization, and/or pharmaceutical coagulants.

It will be appreciated by those skilled in the art that while the invention has been described above in connection with particular embodiments and examples, the invention is not necessarily so limited, and that numerous other embodiments, examples, uses, modifications and departures from the embodiments, examples and uses are intended to be encompassed by the claims attached hereto. To the extent that specific materials are mentioned, it is merely for purposes of illustration and is not intended to limit the invention. One skilled in the art may develop equivalent means or reactants without the exercise of inventive capacity and without departing from the scope of the invention.

The entire disclosure of each patent and publication cited herein is incorporated by reference, as if each such patent or publication were individually incorporated by reference herein. Unless defined otherwise, technical and scientific terms used herein have the same meaning as commonly understood by one of ordinary skill in the art to which this invention belongs. Singleton et al., Dictionary of Microbiology and Molecular Biology 3rd ed., J. Wiley & Sons (New York, N.Y. 2001); March, Advanced Organic Chemistry Reactions, Mechanisms and Structure 5th ed., J. Wiley & Sons (New York, N.Y. 2001); and Sambrook and Russel, Molecular Cloning: A Laboratory Manual 3rd ed., Cold Spring Harbor Laboratory Press (Cold Spring Harbor, N.Y. 2001), provide one skilled in the art with a general guide to many of the terms used in the present application. Various features and advantages of the invention are set forth in the following claims.

REFERENCES

1. The Prevention and Management of Postpartum Haemorrhage: Report of Technical Working Group, Geneva 3-6 Jul. 1989. Geneva: World Health Organization, 1990.
2. Elbourne D R, Prendiville W J, Carroli G, Wood J, McDonald S. Prophylactic use of oxytocin in the third stage of labour. Cochrane Database Syst Rev 2001; (4): CD001808.
3. Bais J M, Eskes M, Pel M, Bonsel G J, Bleker O P. Postpartum haemorrhage in nulliparous women: incidence and risk factors in low and high risk women. A Dutch population-based cohort study on standard (>=500 mL) and severe (>=1000 mL) postpartum haemorrhage. Eur J Obstet Gynecol Reprod Biol 2004; 115:166-72.
4. Reyal F, Deffarges J, Luton D, Blot P, Oury J F, Sibony O. Severe post-partum hemorrhage: descriptive study at the Robert-Debre Hospital maternity ward [French]. J Gynecol Obstet Biol Reprod (Paris) 2002; 31:358-64.
5. Norris T C. Management of postpartum hemorrhage. Am Fam Physician. 1997 Feb. 1; 55 (2):635-40.
6. Fawcus, S, Mbizvo, M, Lindmark, G, Nyström, L. A community-based investigation of maternal mortality from obstetric haemorrhage in rural Zimbabwe. Maternal Mortality Study Group. Trop Doct. 1997 July; 27 (3):159-63.
7. Sultatos L G. Mechanisms of drugs that affect uterine motility. J Nurse Midwifery. 1997 July-August; 42 (4): 367-70.
8. Alexander E. Weingarten, MD, Jeffrey I. Korsh, MD, George G. Neuman, MD, and Steven B. Stern, MD. Postpartum Uterine Atony after Intravenous Dantrolene. Anesth Analg 1987; 66:269-270.
9. Hacker, Neville, J. G. Moore, and Joseph Gambone. Essentials of Obstetrics and Gynecology. 4th ed. Vol. 1. Philadelphia: Elsevier Inc., 2004. 151.
10. Bennie S D, Petrofsky J S, Nisperos J, Tsurudome M, Laymon M. Eur J Appl Physiol. 2002 November; 88 (1-2): 13-9. Epub 2002 Sep. 10. Toward the optimal waveform for electrical stimulation of human muscle.
11. DeLisa, Joel A.; Gans, Bruce M.; Walsh, Nicolas E.; Bockenek, William L.; Frontera, Walter R.; Gerber, Lynn H.; Geiringer, Steve R.; Pease, William S.; Robinson, Lawrence R.; Smith, Jay; Stitik, Todd P.; Zafonte, Ross D. Physical Medicine and Rehabilitation: Principles and Practice. 4th edition. 2004. Lippincott Williams & Wilkins (LWW): Chapter 66.
12. Piallat B, Chabardès S, Devergnas A, Torres N, Allain M, Banat E, Benabid A L. Monophasic but not biphasic pulses induce brain tissue damage during monopolar high-frequency deep brain stimulation. Neurosurgery. 2009 January; 64 (1):156-62; discussion 162-3.

The invention claimed is:

1. A method for treating insufficient uterine contractions after labor and delivery, the method comprising:
generating electrical stimulating current signals at a frequency greater than about 5.0 Hertz;
applying the electrical stimulating current signals to one of a cervix, a vagina, and a uterus during uterine atony after labor and delivery; and
producing uterine tonic contractions that are initiated by the application of the electrical stimulating current signals and are sustained for a time period after the application of the electrical stimulating current signals has been stopped.

2. The method of claim 1 and further comprising conditioning the electrical stimulating current signals to be simultaneously sinusoidal, bi-phasic, and limited to a constant maximum current in order to one of eliminate and reduce tissue damage in tissue through which the stimulating electrical current is applied in one of the cervix, the vagina, and the uterus.

3. The method of claim 1 and further comprising administering additional treatments including one of oxytocin, prostaglandins, misoprostol, prepidil, ergot alkyloids, tamponades, balloon tamponades, sponges, clamps, manual uterine massage and manipulation, sutures, bio-compatible adhesives, cauterization, and pharmaceutical coagulants.

4. The method of claim 1 and further comprising applying the electrical stimulating current signals one of separately, simultaneously, and sequentially to different parts of the uterus, wherein the electrical stimulating current signals include multiple current signals, wherein at least some of the multiple current signals includes different stimulation current parameters in order to one of separately, simultaneously, and sequentially control muscle contraction of the uterus.

5. The method of claim 1, wherein the electrical stimulating current signals are generated with current amplitudes between about 0.01 milliamperes and about 40.00 milliamperes, and current pulse train durations between about 0.01 seconds and about 30 minutes.

6. A method for producing uterine contractions of a patient after labor, the method comprising:
generating electrical stimulating current signals at a frequency greater than about 5.0 Hertz;
applying the electrical stimulating current signals to one of a cervix, a vagina, and a uterus of the patient during uterine atony after labor;

stopping application of the electrical stimulating current signals to one of the cervix, the vagina, and the uterus; and wherein the application and stopping of the electrical stimulating current signals produces global uterine tonic contractions that are sustained after the stopping of the application of the electrical stimulation current signals.

7. The method of claim 6, wherein applying the electrical stimulating current signals to one of the cervix, the vagina, and the uterus of the patient during uterine atony after labor includes applying electrodes across a fundal portion of the uterus and a distal portion of the uterus.

8. The method of claim 6, wherein the application and stopping of the electrical stimulating current signals are performed in a pattern identical to pre-recorded uterine electrical traces obtained from a normally contracting uterus after labor.

9. The method of claim 6 and further comprising monitoring the applied electrical stimulating current signals and modifying at least one of pulse width, current amplitude, pulse train duration, and pulse frequency during the step of generating the electrical stimulating current signals based on the monitored applied electrical stimulating current signals.

* * * * *